(12) United States Patent
Bray et al.

(10) Patent No.: US 7,985,255 B2
(45) Date of Patent: Jul. 26, 2011

(54) IMPLANT SUBSIDENCE CONTROL

(75) Inventors: Robert S. Bray, Studio City, CA (US); James M. Moran, North Royalton, OH (US); Mark T. Whiteaker, Rocky River, OH (US)

(73) Assignee: RSB Spine LLC, Cleveland, OH (US)

( * ) Notice: Subject to any disclaimer, the term of this patent is extended or adjusted under 35 U.S.C. 154(b) by 1246 days.

(21) Appl. No.: 11/248,651

(22) Filed: Oct. 12, 2005

(65) Prior Publication Data

US 2006/0030851 A1    Feb. 9, 2006

Related U.S. Application Data

(63) Continuation-in-part of application No. 10/419,652, filed on Apr. 21, 2003, now Pat. No. 6,984,234.

(51) Int. Cl.
*A61F 2/30* (2006.01)
(52) U.S. Cl. .................. 623/17.11; 623/17.16
(58) Field of Classification Search .................. 606/246, 606/289, 295, 296, 302; 623/17.11, 17.16, 623/17.12–17.15
See application file for complete search history.

(56) References Cited

U.S. PATENT DOCUMENTS

| | | | |
|---|---|---|---|
| 4,503,848 A * | 3/1985 | Caspar et al. ................. | 606/280 |
| 4,904,261 A | 2/1990 | Dove et al. | |
| 5,306,309 A * | 4/1994 | Wagner et al. ............. | 623/17.16 |
| 5,364,399 A | 11/1994 | Lowery et al. | |
| 5,713,898 A | 2/1998 | Stücker et al. | |
| 5,713,899 A | 2/1998 | Marnay et al. | |
| 5,800,433 A | 9/1998 | Benzel et al. | |
| 5,888,223 A * | 3/1999 | Bray, Jr. ...................... | 623/17.16 |
| 6,066,175 A | 5/2000 | Henderson et al. | |
| 6,080,193 A | 6/2000 | Hochshuler et al. | |
| 6,193,721 B1 | 2/2001 | Michelson | |
| 6,200,347 B1 * | 3/2001 | Anderson et al. .......... | 623/16.11 |
| 6,231,610 B1 * | 5/2001 | Geisler ....................... | 623/17.11 |
| 6,245,108 B1 * | 6/2001 | Biscup ....................... | 623/17.11 |
| 6,371,988 B1 * | 4/2002 | Pafford et al. ............. | 623/17.11 |
| 6,413,259 B1 | 7/2002 | Lyons et al. | |
| 6,432,106 B1 * | 8/2002 | Fraser ........................ | 623/17.11 |
| 6,461,359 B1 | 10/2002 | Tribus et al. | |
| 6,524,311 B2 | 2/2003 | Gaines, Jr. | |
| 6,533,786 B1 | 3/2003 | Needham et al. | |
| 6,572,622 B1 | 6/2003 | Schäfer et al. | |

(Continued)

FOREIGN PATENT DOCUMENTS

EP    1103236 A2    11/2000

(Continued)

OTHER PUBLICATIONS

Webster's II New Riverside University Dictionary, 1994, Houghton Mifflin Companty, pp. 413, 1094.*

(Continued)

*Primary Examiner* — Eduardo C Robert
*Assistant Examiner* — Jan Christopher Merene
(74) *Attorney, Agent, or Firm* — Pearne & Gordon LLP

(57) ABSTRACT

An interbody device for the fixation and support of adjacent bone bodies includes a body for implantation at a location between the two vertebrae and one or more protrusions extending from the body. The protrusion(s) are configured for engagement with one of the vertebrae upon implantation and for progressive penetration into the vertebra over a period of time subsequent to the implantation.

98 Claims, 15 Drawing Sheets

U.S. PATENT DOCUMENTS

| | | |
|---|---|---|
| 6,579,290 B1 | 6/2003 | Hardcastle et al. |
| 6,629,998 B1 | 10/2003 | Lin |
| 6,656,179 B1 | 12/2003 | Schaefer et al. |
| 6,730,127 B2 | 5/2004 | Michelson |
| 6,755,833 B1* | 6/2004 | Paul et al. ............... 606/70 |
| 6,837,905 B1 | 1/2005 | Lieberman |
| 6,884,242 B2 | 4/2005 | LeHuec et al. |
| 7,004,944 B2* | 2/2006 | Gause .................. 606/294 |
| 7,041,135 B2 | 5/2006 | Michelson |
| 7,112,222 B2* | 9/2006 | Fraser et al. ........... 623/17.11 |
| 7,163,561 B2 | 1/2007 | Michelson |
| 7,172,627 B2* | 2/2007 | Fiere et al. ............. 623/17.11 |
| 7,232,464 B2 | 6/2007 | Mathieu et al. |
| 7,320,708 B1 | 1/2008 | Bernstein |
| 2001/0005796 A1* | 6/2001 | Zdeblick et al. ........ 623/17.11 |
| 2002/0004683 A1* | 1/2002 | Michelson ............. 623/17.16 |
| 2002/0016595 A1 | 2/2002 | Michelson |
| 2002/0026243 A1* | 2/2002 | Lin ....................... 623/17.11 |
| 2002/0082597 A1 | 6/2002 | Fraser |
| 2002/0087212 A1 | 7/2002 | James et al. |
| 2002/0120273 A1* | 8/2002 | Needham et al. ........... 606/61 |
| 2002/0138142 A1* | 9/2002 | Castro et al. ........... 623/17.11 |
| 2002/0143399 A1* | 10/2002 | Sutcliffe ................ 623/17.11 |
| 2003/0078668 A1* | 4/2003 | Michelson ............. 623/17.16 |
| 2003/0135278 A1* | 7/2003 | Eckman ................ 623/17.14 |
| 2003/0167091 A1 | 9/2003 | Scharf |
| 2003/0225409 A1 | 12/2003 | Freid et al. |
| 2004/0127902 A1 | 7/2004 | Suzuki et al. |
| 2004/0193269 A1 | 9/2004 | Fraser et al. |
| 2004/0204712 A1 | 10/2004 | Kolb et al. |
| 2004/0236333 A1 | 11/2004 | Lin |
| 2005/0101960 A1* | 5/2005 | Fiere et al. ................ 606/72 |
| 2005/0177236 A1 | 8/2005 | Mathieu et al. |
| 2006/0030851 A1 | 2/2006 | Bray et al. |
| 2006/0085071 A1 | 4/2006 | Lechmann et al. |
| 2008/0177307 A1* | 7/2008 | Moskowitz et al. ......... 606/246 |
| 2010/0057206 A1* | 3/2010 | Duffield et al. ............ 623/17.16 |
| 2010/0087925 A1* | 4/2010 | Kostuik et al. ............ 623/17.16 |
| 2010/0145459 A1* | 6/2010 | McDonough et al. ..... 623/17.16 |
| 2010/0145460 A1* | 6/2010 | McDonough et al. ..... 623/17.16 |

FOREIGN PATENT DOCUMENTS

| | | | |
|---|---|---|---|
| EP | 1247503 | | 10/2002 |
| WO | 9720526 | | 6/1997 |
| WO | 9856319 | | 12/1998 |
| WO | WO 98/58604 | | 12/1998 |
| WO | 9927864 A2 | | 6/1999 |
| WO | 0007527 | | 2/2000 |
| WO | 0066011 | | 11/2000 |
| WO | 0066045 | | 11/2000 |
| WO | WO 00/66045 | * | 11/2000 |
| WO | WO /0126566 | * | 4/2001 |
| WO | 0180785 A1 | | 11/2001 |
| WO | 0195837 | | 12/2001 |
| WO | 0203885 A2 | | 1/2002 |
| WO | WO 03/005938 | | 1/2003 |
| WO | WO 2004/069106 | | 8/2004 |

OTHER PUBLICATIONS http://reference.dictionary.com, accessed Jul. 29, 2009 for definition of opposite.* http://www.thefreedictionary.com, definition for elongate, accessed on Feb. 23, 2010.* http://www.thefreedictionary.com, definition for slender, accessed on Feb. 23, 2010.*

International Search Report (PCT/US2007/087108) dated Dec. 15, 2008.

* cited by examiner

IMPLANT SUBSIDENCE CONTROL

RELATED PATENT APPLICATION

Priority is claimed from U.S. Pat. No. 6,984,234, the disclosure of which is expressly incorporated herein.

BACKGROUND OF THE INVENTION

1) Field of the Invention

The present invention relates generally to devices for the fixation and support of bone bodies. In particular, the present invention relates to an implant device, such as an interbody fusion device, having subsidence control.

2) Background of the Invention

Bone mechanical properties greatly influence the stiffness of vertebra-implant-vertebra constructs. Bone properties are a function of many factors including bone mineral density, age, and sex. For comparative purposes, it will be assumed that bone properties are constant in the following discussions. Preparation of the bone to receive the implant can influence strength and stiffness. Again, for comparative purposes, it will be assumed that bone preparation is not a variable except when specifically discussed.

Interbody devices are typically classified as threaded cylinders or screws (e.g., BAK C), boxes (usually tapered rectangular boxes with ridges like the Brantigan cage), or vertical cylinders (e.g., Harms cage). Threaded cylinders usually have small pores and graft material is located inside the hollow interior of the cylinder. Device stiffness might be an issue for such designs. Boxes and vertical cylinders are generally open structures and in these devices a combination of device stiffness and subsidence are responsible for loading the graft.

The stiffness of a material and the stiffness of the structure (device) are often confused. Material stiffness is quantified by Modulus of Elasticity, the slope of the stress-strain curve. Steel has a high modulus, and gold has a low modulus. Structural or device stiffness is a function of dimensions of the part and the material from which the part is made. For example, steel is a very stiff material. However, when formed into the shape of a structure like a paperclip it is easily bent. Stiffness of an assembly or construct can be influenced by connections. While a paperclip and even a piece of paper are strong in tension, when assembled with a piece of paper a paperclip can be easily pulled off because they are only held together by friction.

The same analogy holds for inter-vertebral implants. For instance, consider a simplified construct consisting of a bone block, an interbody device, and a bone block, stacked on top of each other and loaded in compression. If the device is made from a low modulus material but has a large footprint on the bone, and conforms very well to the bone, the assembly can be very stiff in compression. The slope of the load-deflection curve would be steep. A device made from a high modulus material that has a small footprint on the bone and sharp edges might simply punch into the bone under compressive load. The slope of the load-deflection curve would be low, making the construct appear very compliant despite the fact that the device is rigid.

Finally, the terms flexibility and stiffness are used in connection with both the range of motion of the spine and the mechanical performance of implant constructs, and the distinction is not always clearly defined.

BRIEF SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In accordance with an aspect of the present invention, an interbody device is provided. The interbody device includes a base member having a plurality of interface members extending from a portion of the base member, the interface members configured to provide controlled subsidence of the interbody device into a bone body. The interbody device also includes a plurality of bone fasteners extending through apertures provided in the base member; and restraining means for restricting movement of at least one of the plurality of bone fasteners.

In accordance with another aspect of the present invention, an interbody device includes: a base member configured for insertion between two adjacent bone bodies; controlled subsidence means extending from the base member, the controlled subsidence means configured to provide penetration of the base member into at least one of the bone bodies with increased resistance to subsidence; and means for fastening the base member to the two adjacent bone bodies.

In accordance with yet another aspect of the present invention, an interbody device includes a base member configured for insertion between two adjacent bone bodies. The base member includes: a plurality of interface members extending from a surface of the base member, the plurality of interface members configured to penetrate into at least one surface of at least one of the body bodies with increased resistance to subsidence; at least one angled hole extending therethrough for receiving a bone fastener; and at least one elongated slot extending therethrough for receiving a bone fastener, the elongated slot configured to permit the corresponding bone fastener to slide within the slot.

In accordance with yet another aspect of the present invention, a device for fixation and support of bone bodies includes: a body configured to interface with two or more bone bodies; and at least one interface member extending from the body, wherein the at least one interface member is configured to provide a controlled subsidence of the body into at least one of the two or more bone bodies.

In accordance with yet another aspect of the present invention, a device for fixation and support of bone bodies is provided. The device includes: means for interfacing between two or more bone bodies; and means for providing a controlled subsidence of the device into at least one of the two or more bone bodies in accordance with a desired subsidence profile.

In accordance with yet another aspect of the present invention, a device for securing two adjacent spinal vertebrae is provided. The device includes: a body for implantation at a location between the two vertebrae; and at least one protrusion extending from the body for engagement with one of the vertebrae upon implantation and for progressive penetration into the vertebra over a period of time subsequent to the implantation.

In accordance with yet another aspect of the present invention, a method of securing two adjacent spinal vertebrae with a device is provided. The method comprises: implanting a body of the device at a location between the two vertebrae; engaging at least one protrusion extending from the body for with one of the bone members upon implantation progressively penetrating the protrusion into the vertebra over a period of time subsequent to the implantation.

In accordance with yet another aspect of the present invention, an interbody device for securing two adjacent bone members includes: a base member for implantation at a location between the two bone members; and means for maintaining the base member within the implant location between the bone members; wherein the base member includes at least one protrusion for engagement with one of the bone members upon implantation and for progressive penetration over a period of time subsequent to the implantation.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

The foregoing and other features and advantages of the present invention will become apparent to those skilled in the art to which the present invention relates upon reading the following description with reference to the accompanying drawings.

DESCRIPTION OF EXAMPLE EMBODIMENTS

Figure 1:
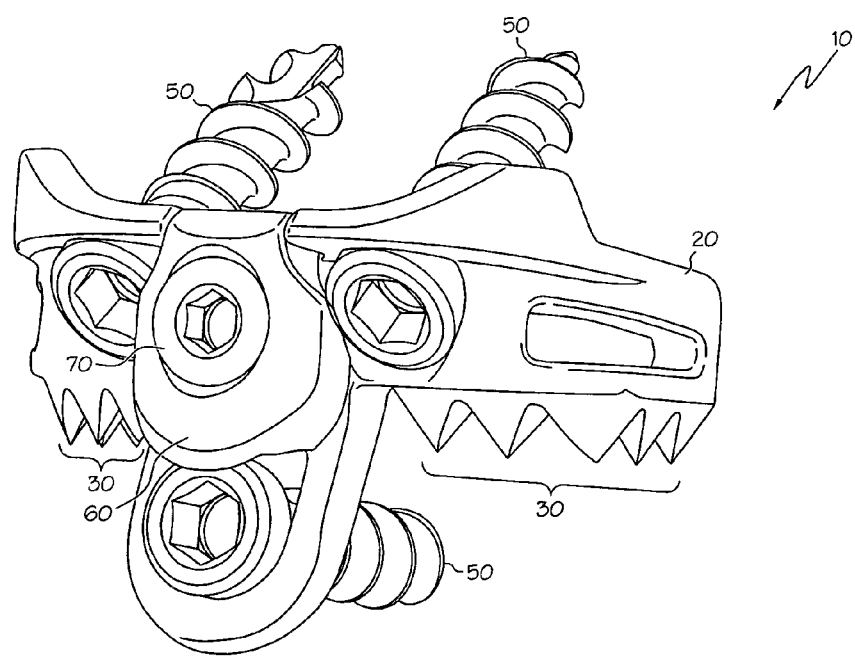
FIG. 1 is a front perspective view of an interbody device in accordance with an aspect of the present invention.

The present invention relates to an implant device, such as an interbody device, having subsidence control. The present invention will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

Figure 2:
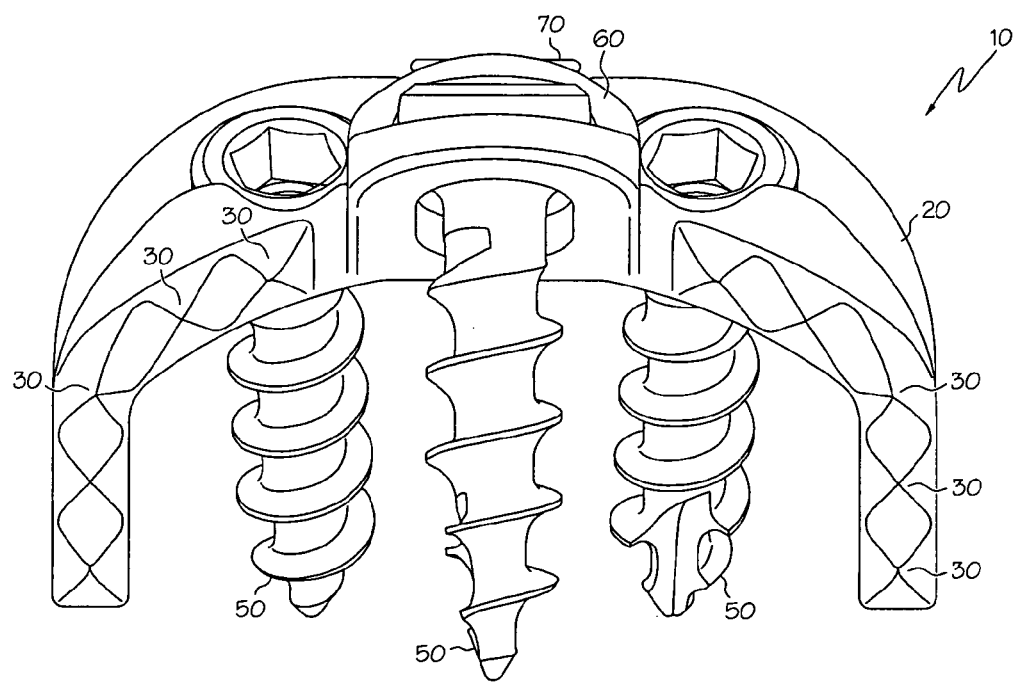
FIG. 2 is a bottom perspective view of an interbody device in accordance with an aspect of the present invention.
Figure 3:
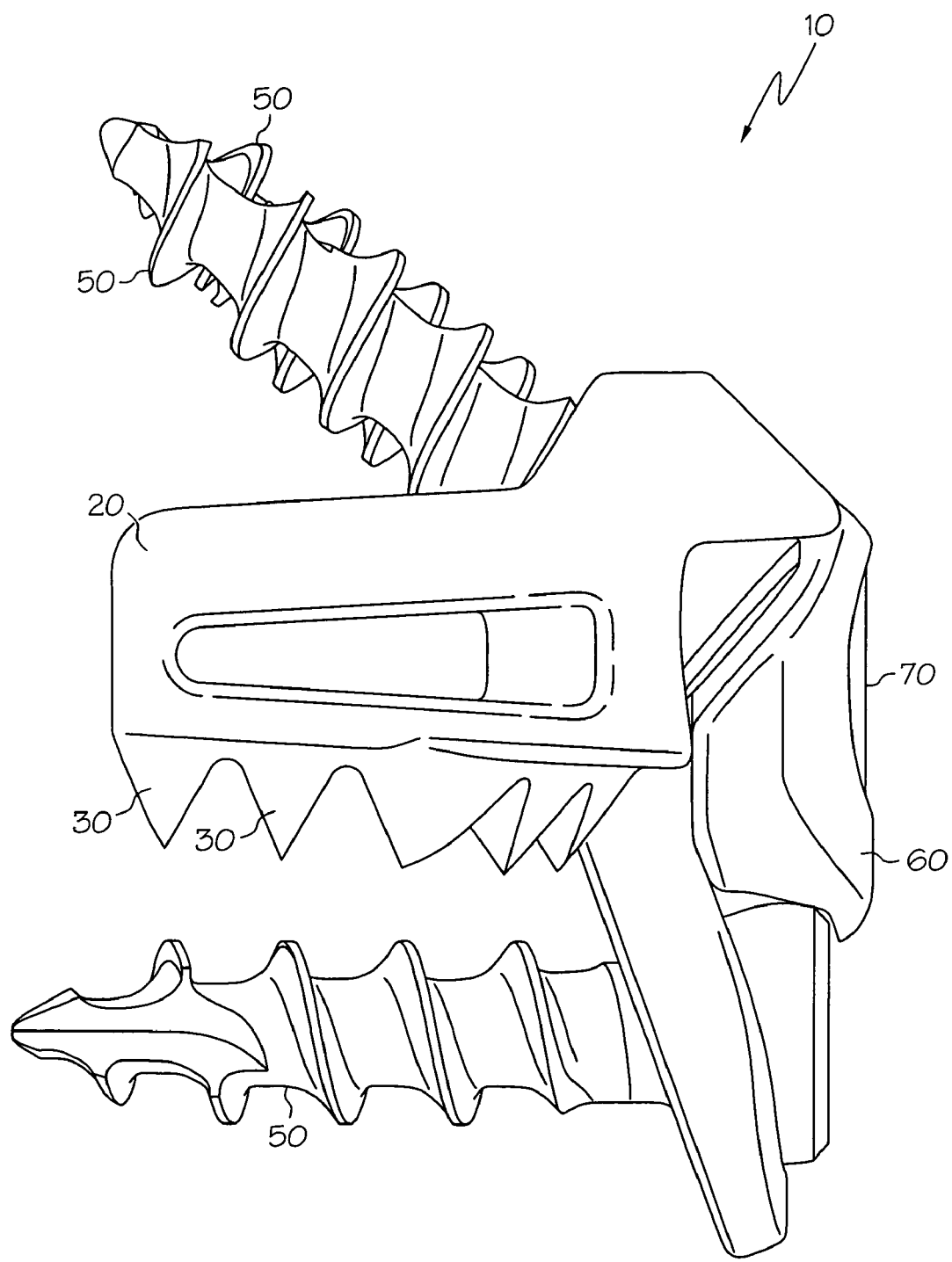
FIG. 3 is a side view of an interbody device in accordance with an aspect of the present invention.

Referring initially to FIGS. 1-3, an example of an interbody device 10 is illustrated in accordance with an aspect of the present invention. The interbody device 10 is configured to fix and secure two bone bodies. As used herein, the phrase "bone bodies" is intended to include individual bones as well as fragments or portions of bones. More specifically, and as will be described in further detail below, the interbody device can fix and secure adjacent vertebrae that have had cartilaginous disc between the vertebrae replaced with a graft of bone tissue or some other material that promotes the fusion of the vertebrae It is to be appreciated that one aspect that is addressed by the present invention is load sharing with a graft. The configuration of the interbody device 10 includes a base member 20 having a plurality of protrusions or interface members 30 extending from a portion of the base member 20. As will be explained in further detail below, the interface members 30 are configured to contact at least one surface of at least one bone body to provide subsidence control for the interbody device 10. Controlled subsidence relates to resistance to subsidence and total amount of subsidence. The base member 20 of the interbody device 10 also includes a plurality of apertures, each of which is configured to receive a corresponding bone fastener 50 therethrough.

The interbody device 10 also includes a restraining means for restricting movement of one or more bone fasteners 50 coupled to the base member 20. The restraining means can be any means for securely covering at least a part of each of the bone fasteners 50 so that the bone fasteners 50 cannot back out from the bone bodies once screwed in through the base member 20 of the device 10. In the depicted embodiment, the bone screw restraining means comprises a restraining plate 60 and a restraining plate fixing means 70.

Turning now to FIGS. 4-7, the base member 20 of the interbody device 10 is illustrated in greater detail. The base member 20 is generally u-shaped with a first end 80 at the open end of the u-shape and a second end 90 at the closed end of the u-shape (see FIGS. 6 and 7). The second end 90 includes a primary member 100 and a secondary member 110, which extends from and is angled relative to the primary member 100. First and second legs 120, 130 of the u-shaped base member 20 are integrally formed with the primary member 100. In use, the first and second legs 120, 130 extend around a bone graft to mitigate lateral shift of the graft and control subsidence of adjacent vertebrae as they set during fusion.

Subsidence is further controlled by the presence of the interface members 30 that extend from a portion of the base member 20. The interface members 30, as depicted in the present embodiment, can include a plurality of teeth extending from bottom surfaces of the primary member 100, the first leg 120, and the second leg 130. Accordingly, when coupled with the bone bodies, the interface members 30 extend from the base member 20 in a direction that is aligned with an elongate direction of the spine. The interface members 30 thus, are configured to provide a progressive penetration into the bone body over a period of time in a direction aligned with the elongate direction of the spine. Thus, the alignment within the elongate direction prevents thrust force transverse to the elongation direction (e.g., in the lateral (side-side) or anterior-posterior (front-back) directions). It is to be appreciated, however, that any suitable configuration of interface members can be provided at any suitable location on the base member that interfaces with a surface of the bone body.

The interface members can include teeth, knife-edges, spikes, posts, pegs, and the like, including any combination thereof. Within the example shown within the Figures an example projections that are substantially shaped as a four-sided pyramid is shown (see for example FIGS. 4-7 to see the shape). The configuration of the interface members includes interlocking external features that impact a subsidence profile, which is a relationship between an applied load and an amount of settling the interbody device 10 experiences when secured to the bone bodies. Or in other words, the subsidence profile is a relationship between a depth of subsidence of the interface members and a force required to achieve the depth of subsidence. When first implanted, the interface members 30 will rest on top of the bone surface. When load is applied to the interbody device 10, the interface members 30 will penetrate, or subside, into the bone in a controlled manner. The interface members can dig into the bone "fast" initially and then slow down as more of the tooth cross section embeds. Different interface member configurations provide different controlled subsidence profiles. The density of the bone body also impacts the subsidence profile. For example, in a lower density bone body representation, such as 15 pcf, the interface members can penetrate the bone body by about 1 mm using between about 50-100 N of force and by about 2 mm using between about 150-250 N of force. In a medium density bone body, such as 20 pcf, the interface members can penetrate the bone body by about 1 mm using between about 100-200 N of force and by about 2 mm using between about 400-900 N of force. In a higher density bone body, such as 40 pcf, the interface members can penetrate the bone body by about 1 mm using between about 100-500 N of force and by about 2 mm using between about 1000-2250 N of force. The amount of force needed for displacement and the rate of penetration of the interface members into the bone body depends, in part, upon the configuration of the interface members. It should be noted that all of the pcf densities refer to polyurethane foam (which is referenced to ASTM standards) that is used as a bone analog for test purposes. The tests were also conducted using a straight test "blade" that was 40 mm long, not an actual implant. Also, as mentioned there is no thrust in a direction transverse to the elongation direction of the spine. As can be appreciated from the drawings that the pyramid-shaped members 30 are pointed along the elongate direction and each opposed pair of sides of the pyramid are symmetrical to each other. Also, bisecting a pyramid-shaped member 30 through planes bisecting the sides results in the member being substantially symmetrical. For example, such bisection down the middle of the member cutting sides in two results in substantial symmetry. Moreover a similar bisection perpendicular (i.e., rotated 90°) to the aforementioned bisection also results in substantially symmetrical bisection of the member. Accordingly, at least one of the members 30 is substantially symmetrical in each of two perpendicular directions. Similarly, bisecting a pyramid-shaped member 30 along its vertices results in substantially symmetry on either side of the bisections. So again, such bisecting a pyramid-shaped member 30 through planes results in the member being substantially symmetrical. Such substantial symmetry thus provides for substantially symmetrical penetrating force. As mentioned, the projections may have different shapes. If a shape that is not substantially symmetrical in each of two directions, such as a sawtooth, a substantially symmetrical penetrating force would not be provided.

Figure 4:
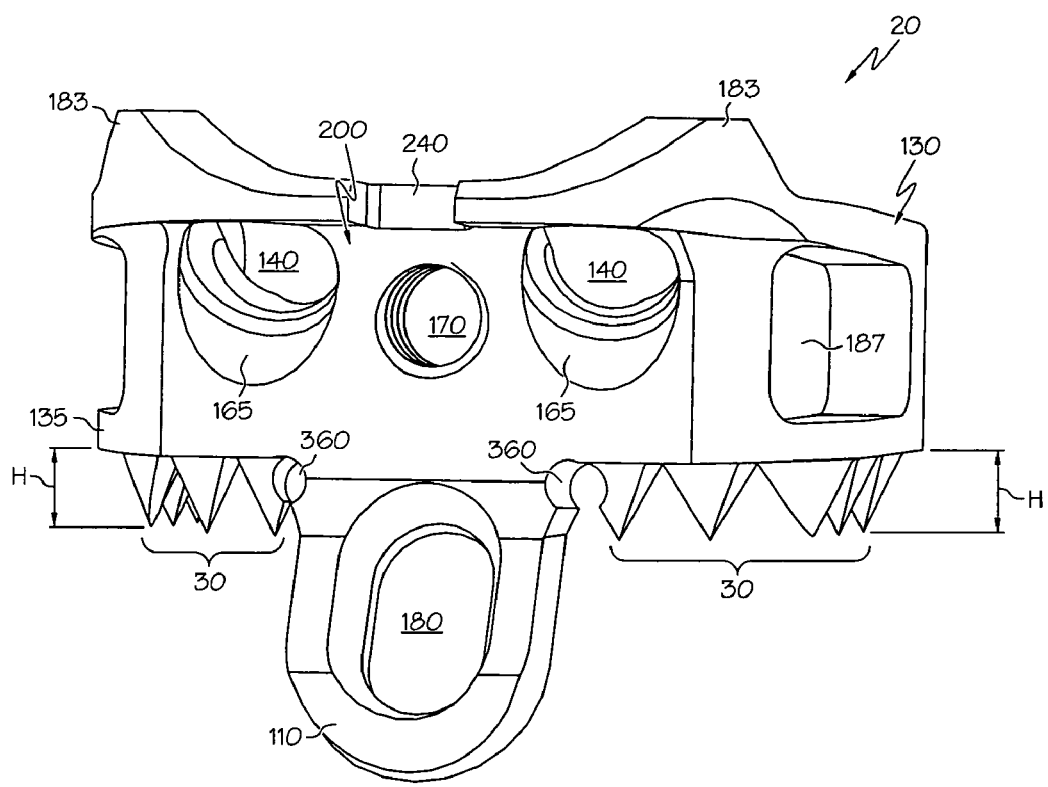
FIG. 4 is a front perspective view of a base member of an interbody device in accordance with an aspect of the present invention.

The height (H) of the interface members 30 determines a depth of penetration into the bone body (see FIG. 4). Generally, when the interbody device 10 has subsided to a point where the interface members are fully embedded in the bone, the applied load will be distributed across the entire surface of the interbody device 10 and subsidence will cease. Typically, the screw will be at the end of the slot. Thus, the height (H) of the interface members can control an amount of subsidence that the interbody device 10 will permit.

In addition to the height (H) of the interface members 30, the shape of the interface members 30 also affects subsidence of the interbody device 10. The shape of the interface members 30 controls a shape of the subsidence profile; and therefore, affects the load shared with the graft material. For instance, if the interface members 30 were limited to a few sharply pointed spikes, subsidence would occur substantially immediately and the interbody device 10 would rapidly seat in the bone to the fullest extent under low force. In this instance, any graft material would be immediately and highly loaded. Such immediate subsidence is not desirable because the joint space could narrow and cause nerve root or spinal cord compression. Also, the graft would be overloaded, inhibiting fusion. However, some subsidence is needed to load the graft and ensure fusion. Accordingly, by configuring the interface members 30 to have a broadly shaped portion, the interbody device 10 has increased resistance to subsidence as the interface members 30 penetrate into the bone body; and the graft material is gradually loaded as the device subsides. For instance, turning to FIG. 7, each tooth 30 is shaped with a substantially broad base, the base being defined by a length (L) and width (W) of each tooth. The substantially broad base of each tooth facilitates controlled subsidence of the interbody device 10. For instance, the as the tooth becomes wider in cross section, the penetration of the tooth into the bone body will become slower.

Once the interface members 30 have fully penetrated the bone, the surface area of the base member 20 is of an area large enough to resist further subsidence of the interbody device 10. To increase subsidence resistance, at an interface between the a plurality of teeth 30 and the bottom surfaces of the primary member 100 and the first and second legs 120, 130, a shelf-like area 135 is created. The shelf-like area 135 provides an extended surface area to contact the bone material, thereby increasing subsidence resistance once the interface members 30 have fully subsided. As mentioned, the screw will typically be at the end of the slot.

Figure 5:
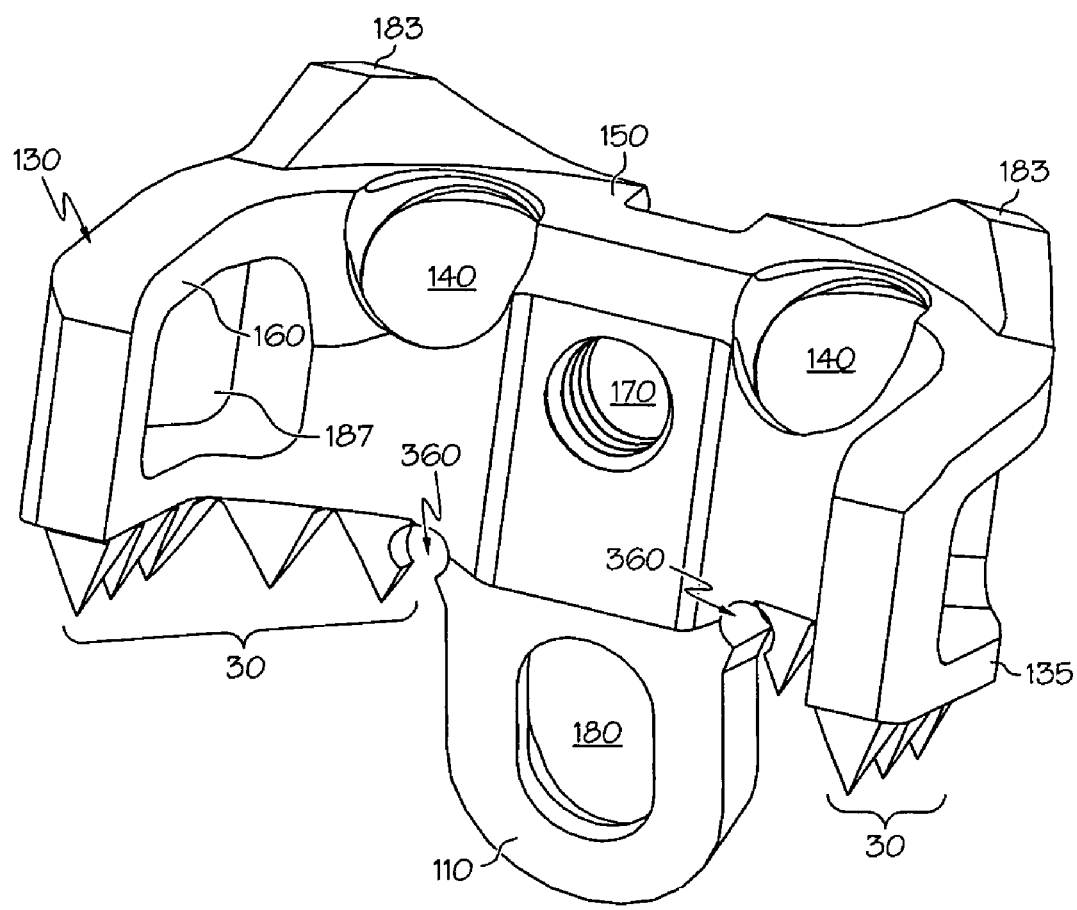
FIG. 5 is a back perspective view of a base member of an interbody device in accordance with an aspect of the present invention.
Figure 6:
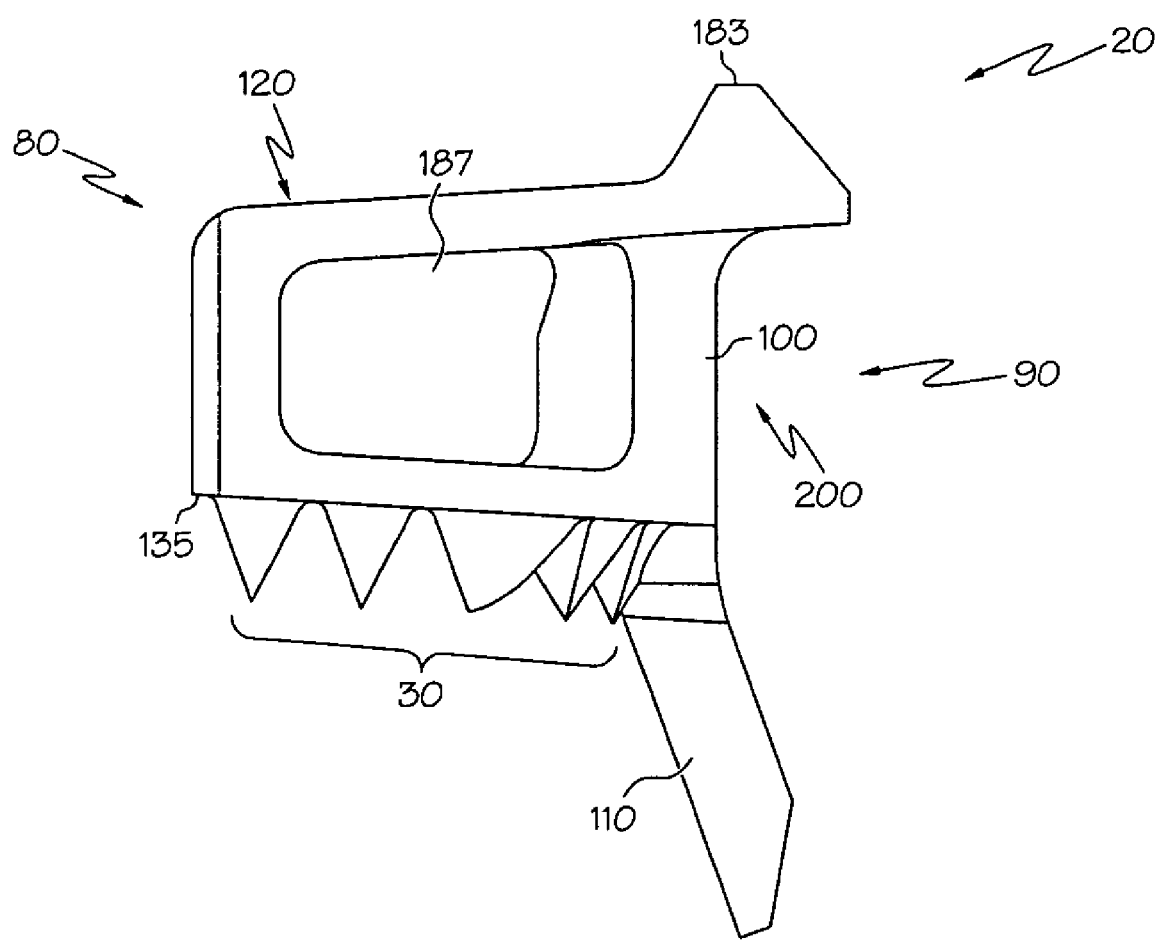
FIG. 6 is a side view of a base member of an interbody device in accordance with an aspect of the present invention.
Figure 7:
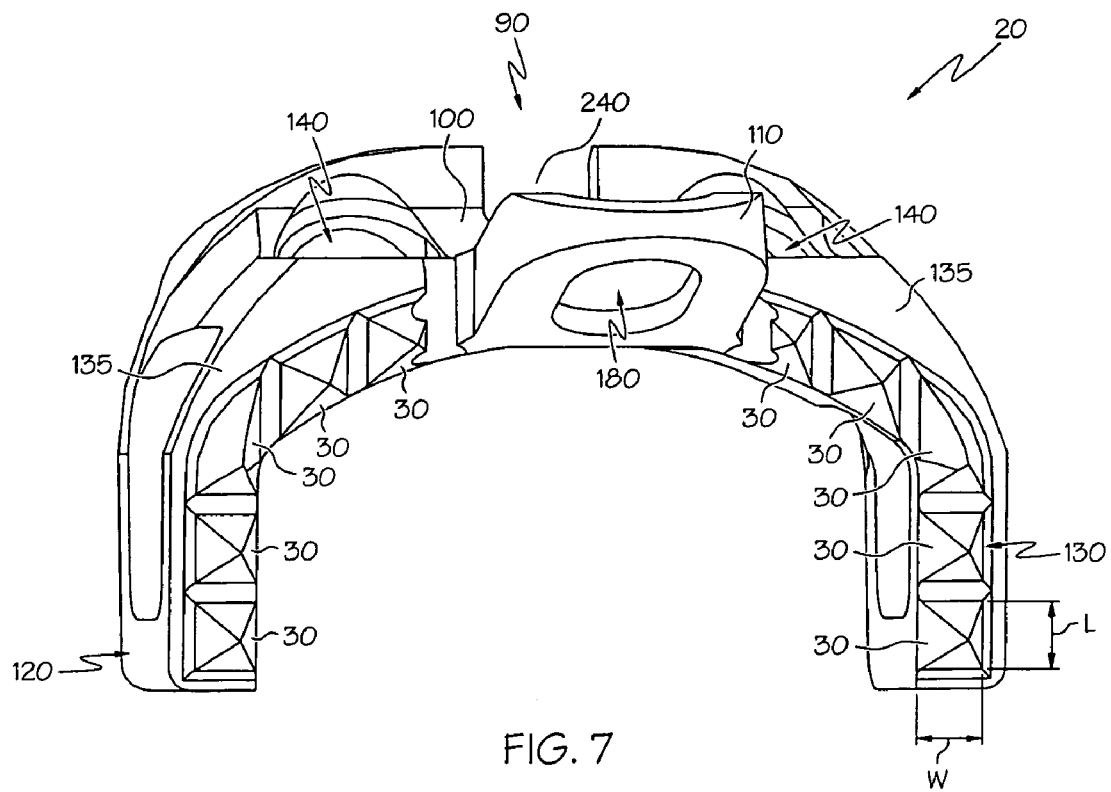
FIG. 7 is a bottom perspective view of a base member of an interbody device in accordance with an aspect of the present invention.

Turning back to the primary and secondary members 100, 110 of the base member 20, the secondary member 110 has a front surface that is generally continuous with a front surface of the primary member 100, as illustrated in FIG. 4 and a back surface that is generally continuous with a back surface of the primary member 100, as illustrated in FIG. 5. FIG. 6 illustrates the angular relationship between the primary and secondary members 100, 110. The primary member 100 and secondary member 110 are arranged relative to each other so that their front surfaces form an angle greater than 90° and less than 180°, preferably from 110° to about 160°. As will become apparent, the angle at which the primary and secondary members 100, 110 are joined is provided so that bone screws can be introduced through the base member 20 at desired angles, as discussed further below. Accordingly, the base member 20 can be designed in any other manner that permits the bone screws to be introduced therethrough at the desired angles.

The primary member 100 includes at least one, and preferably two (as shown in the depicted embodiment) first bone screw holes 140 extending therethrough, each configured to receive a corresponding bone screw. The first bone screw holes 140 in the primary member 110 are configured such that bone screws extend through the holes 140 at an angle, as illustrated in FIG. 3. For example, the first bone screw holes 140 can extend through a corner that joins a top surface 150 of the base member 20 to a back surface 160 of the base member 20, as best shown in FIG. 5. As a result, each bone screw extending through the first bone screw holes 140 can enter the bone body at an angle, as discussed further below. Each of the first bone screw holes 140 is sufficiently large to allow a portion of a respective bone screw to pass therethrough but not large enough to allow a retaining portion of the bone screw through, such as the head of the bone screw. Further, each of the first bone screw holes 140 has a seat 165 on which the retaining portion of a respective bone screw rests. Each seat 165 has a generally concave spherical shape and the surface of the retaining portion of the bone fastener in contact with the seat 165 has a complementary convex spherical configuration. Consequently, the bone screws are free to pivot on the seats 165. The primary member 100 also includes a threaded hole 170 for receiving the restraining member fastener 70.

The secondary member 110 includes a second bone screw hole 180 in the form of an elongated slot for receiving a bone screw. The bone screw is introduced into the second bone screw hole 180 and into a second bone body. The second bone screw hole 180 is configured such that a bone screw can slide and rotate within the slot relative to the base member 20 and generally toward the primary member 100. Thus, in use, as two adjacent bone bodies, to which the base member 20 is fixed, collapse or settle and move toward each other, the bone screw contained within the second bone screw hole 180 will slide within the slot and move with the bone body into which it extends in a direction toward the primary member 100 and the other bone body. The sliding aspect of the movement of the bone screw along the elongate slot is a translation movement and is in distinction from a pivoting movement. In other words, the translational sliding aspect is the non-pivoting aspect.

At least one and preferably two projections 183 extend upwardly from the top surface 150 of the base member 20. The projections 183 contact a surface of the bone bodies to provide a stop when inserting the base member 20 between the bone bodies. The base member 20 also includes holes 187 provided through each of the first and second legs 120, 130. The holes 187 facilitate visualization of the fusion mass on x-rays and bone growth therethrough when the interbody device 10 is positioned between two bone bodies.

The base member 20 may be made of any suitable material, and is preferably made from titanium or a titanium alloy. The thickness of the base member 20 is not critical, and preferably ranges from about 1 mm to about 2 mm, and more preferably is about 1.6 mm. The height of the base member 20 will depend on the needs of the particular patient.

Figure 8:
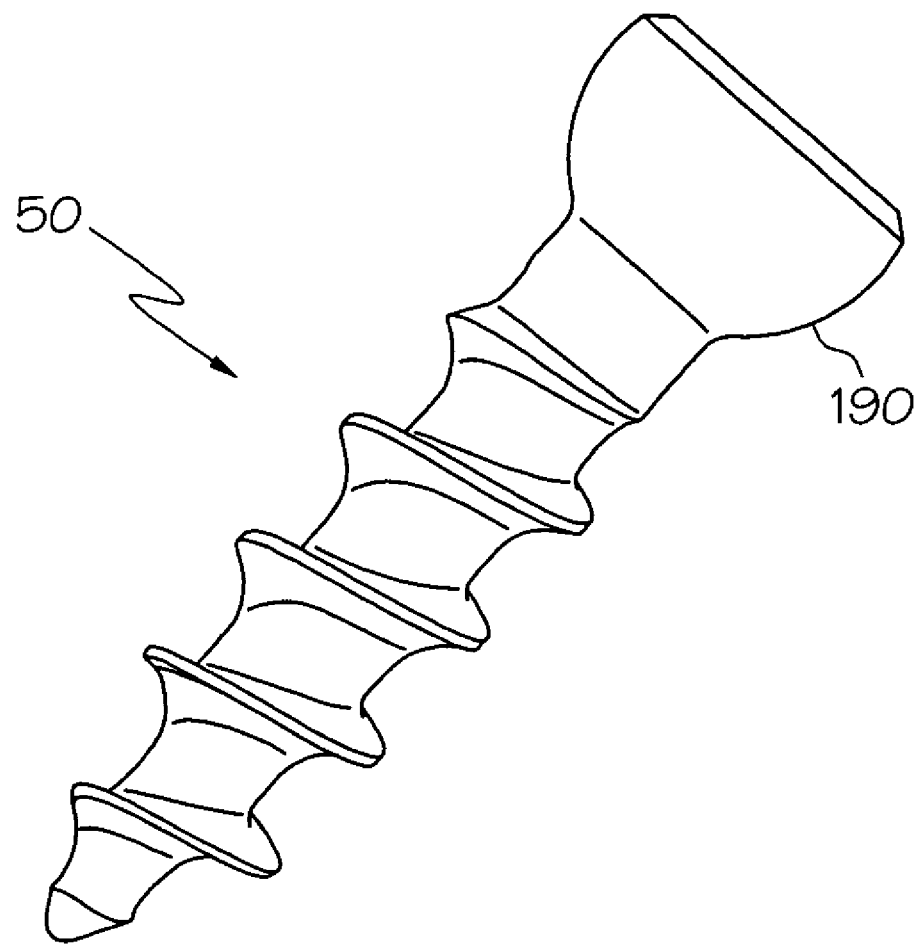
FIG. 8 is a perspective view of a bone screw of an interbody device in accordance with an aspect of the present invention.

Turning now to FIG. 8, the bone fastener 50 is illustrated in further detail in accordance with an aspect of the present invention. The bone fastener 50 can comprise a bone screw, a plurality of which is used for securing the interbody device 10 to the bone bodies. The bone fasteners 50 can be made of any suitable material, and are preferably made of the same material as the base member 20, such as titanium or a titanium alloy. The bone fasteners 50 can all have the same shape, such as that shown in FIGS. 1-3. In the depicted example, the bone fasteners each have a radiused head 190. As used herein, the term "radiused head" means that the lower portion of the bone screw head, i.e., the portion that is nearest the shank, is generally rounded, to thereby permit the bone screws to toggle within their respective holes 140 and 180. The bone fasteners 50 can have any other suitable shape that permits them to cooperate with the first and second bone screw holes 140 and 180.

Figure 9:
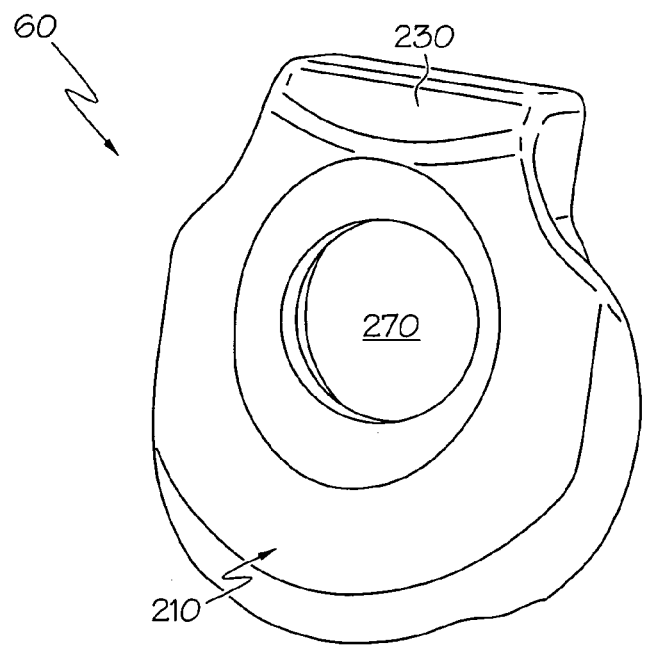
FIG. 9 is a front perspective view of a restraining member of an interbody device in accordance with an aspect of the present invention.
Figure 10:
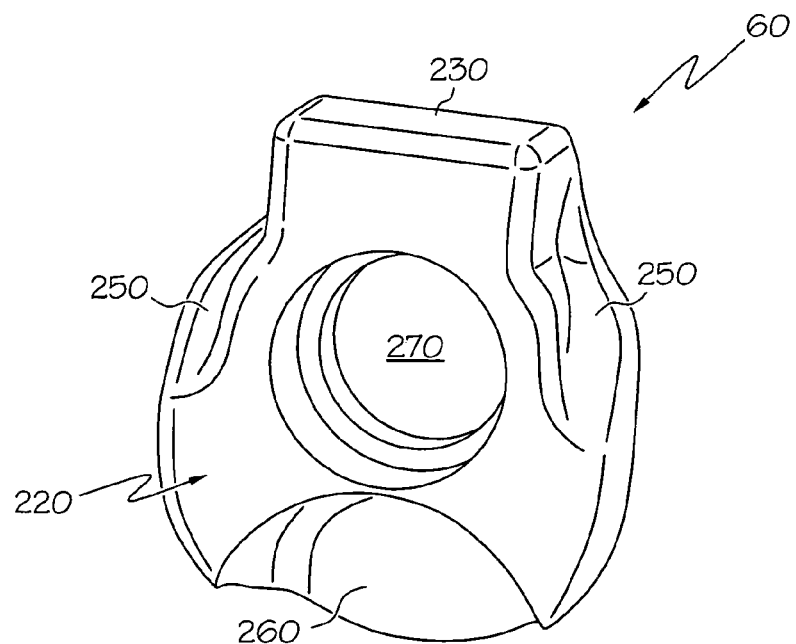
FIG. 10 is a back perspective view of a restraining member of an interbody device in accordance with an aspect of the present invention.

The bone fasteners are secured to the base member 20 via restraining means. As stated above, the restraining means can include a restraining plate 60, an example of which is illustrated in FIGS. 9 and 10 in accordance with an aspect of the present invention. The restraining plate 60 is configured to correspond with a recessed region 200 of the base member 20 of the interbody device 10 (see FIGS. 4 and 6). More specifically, the restraining plate 60 includes a generally rounded front side 210 and a generally flat back side 220. The restraining plate 60 has a flange 230 formed in a top portion of the plate, the flange 230 being configured to fit within a corresponding groove 240 formed in the base member 20. The use of the recessed region 200 and the groove 240 in the base member 20 facilitates proper positioning of the restraining plate 60 on the base member 20. The thickness of the restraining plate 60 is not critical, but should generally be as thin as possible. Some example thicknesses are preferably in the range from about 0.5 mm to about 2 mm, more preferably from about 1 mm to about 1.5 mm.

Turning to FIG. 10, the restraining plate 60 includes a plurality of notches formed along the edges of its back surface 220. The notches include at least one generally rounded notch 250, preferably two, each of the generally rounded notches 250 configured to correspond with one of the bone screws 50. When the restraining plate 60 is fixed in place over the base member 20, the generally rounded notches 250 each cover a portion of a corresponding one of the bone screws 50. The notches 250 are generally rounded so as to permit the bone screws 50 to toggle within the first bone screw holes 40. The restraining plate 60 also includes a substantially U-shaped notch 260, which is curved outwardly towards the edge of the restraining plate 60. When the restraining plate 60 is fixed in place over the base member 20, the top of the bone screw 50 positioned within the second bone screw hole 180 sits within the U-shaped notch 260. Thus, a top of the bone screw 50 is covered by the top surface of the restraining plate 60. With this design, the bone screw 50 positioned within the second bone screw hole 180 is permitted to slide and toggle within the slot even when the restraining plate 60 is fixed over the bone screw 50.

The restraining plate 60 also includes an aperture 270 formed therethrough. The aperture 270 in the restraining plate 60 is aligned with a hole 170 in the primary member 110 of the base member 20, both of which can receive a restraining member fastener 70 for fixing the restraining plate 60 in place over the base member 20. The restraining member fastener 70 can be made of any suitable material well known in the art, preferably titanium or a titanium alloy. The restraining member fastener 70 can be a screw, such as a hexagonal screw that can be turned with a hexagonal driver. Other types of fasteners can also be used, as well as any other suitable mechanism for fixing the restraining plate 60 to the base member 20. The precise mechanism by which the restraining plate 60 is fixed to the base member 20 is not critical to the invention.

Additionally, it is to be appreciated that any other suitable bone screw restraining means can be used in connection with the present invention. For example, the bone screw restraining means can comprise multiple restraining plates that cover different bone screws. Alternatively, the bone screw restraining means can comprise one or more screws with heads that overlap at least a portion of one or more bone screws to thereby prevent the bone screws from backing out.

Figure 11:
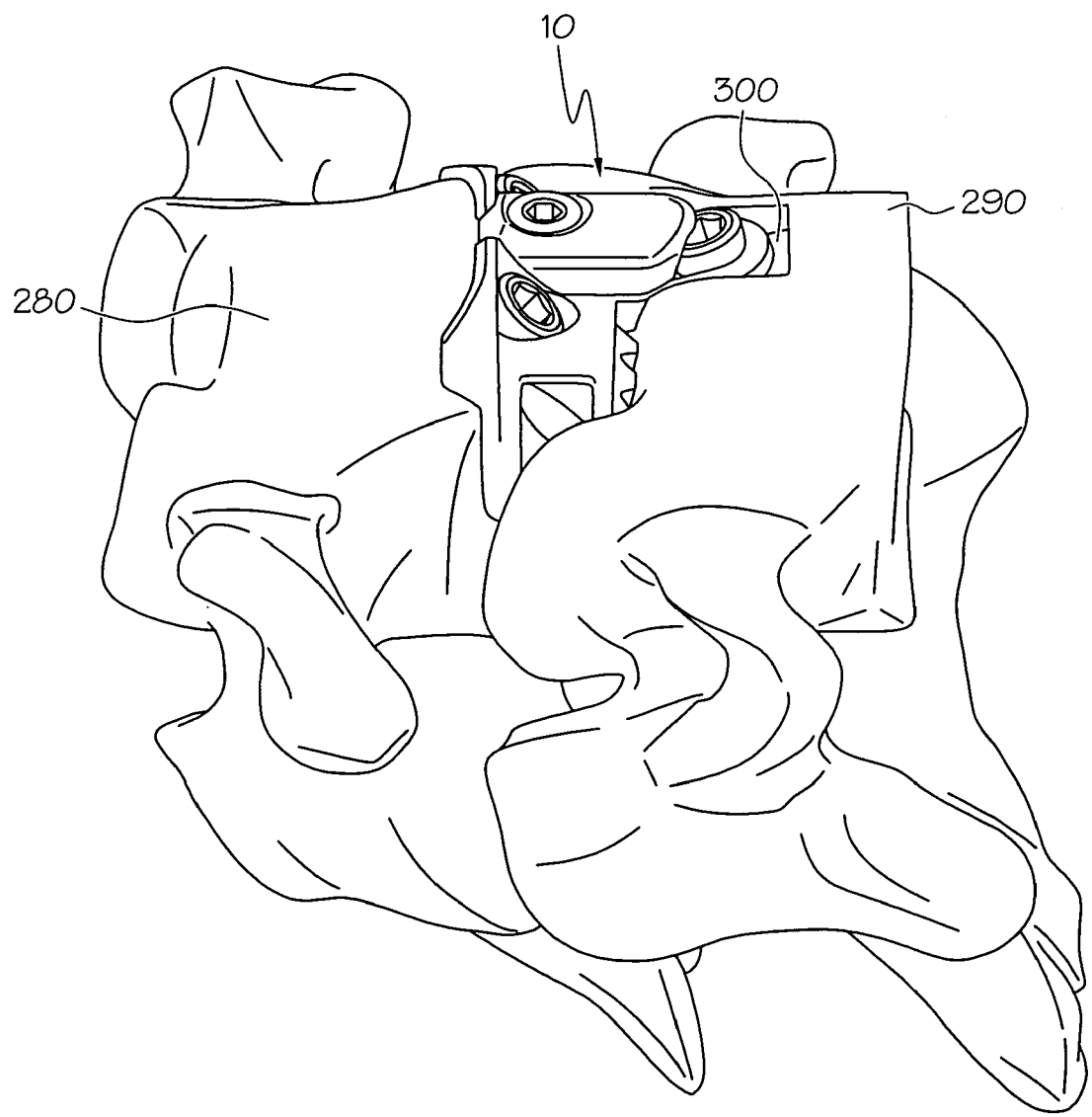
FIG. 11 is a side perspective view of an interbody device positioned between two bone bodies in accordance with an aspect of the present invention.
Figure 12:
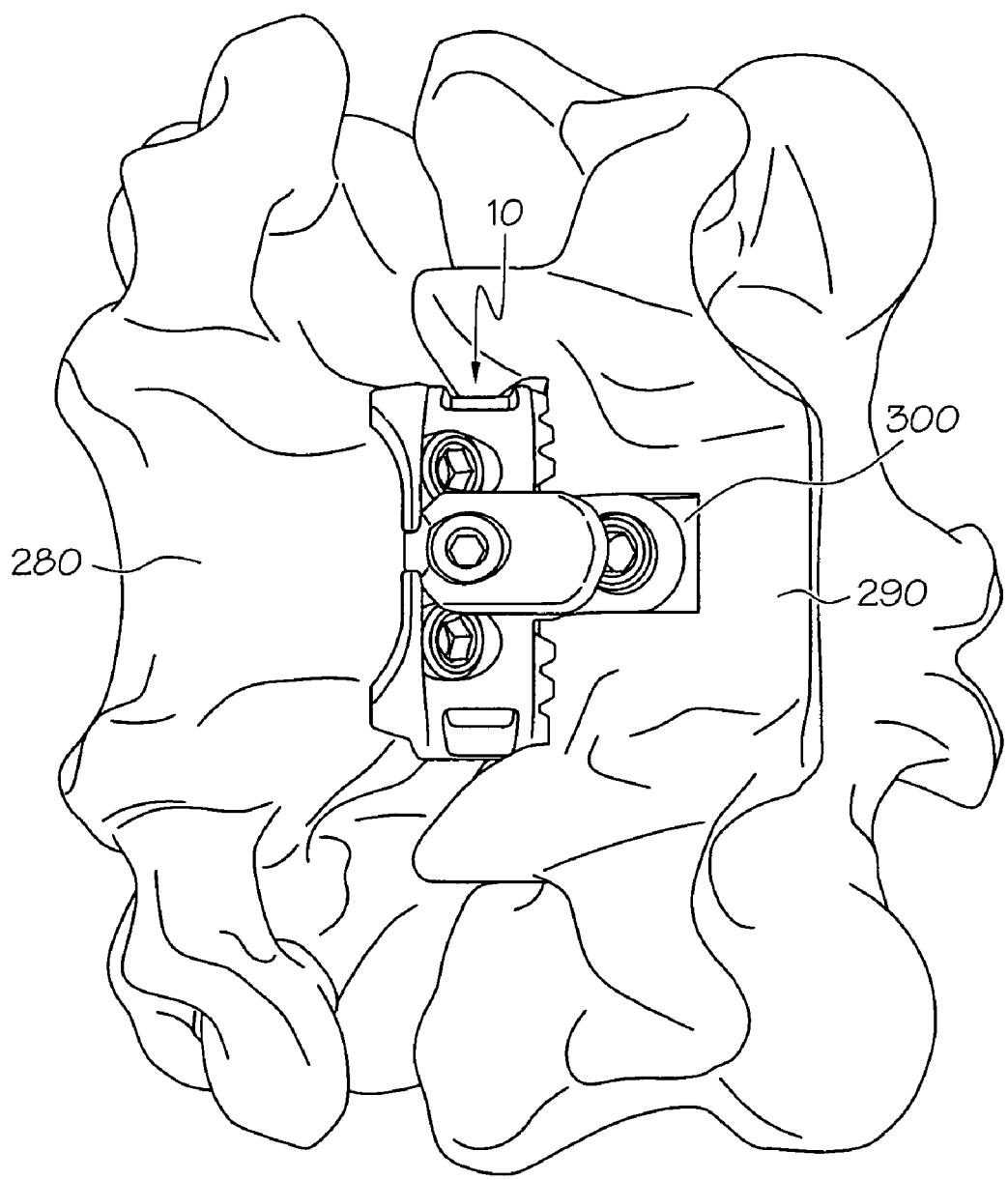
FIG. 12 is a top perspective view of an interbody device positioned between two bone bodies in accordance with an aspect of the present invention.

FIGS. 11 and 12 illustrate the interbody device 10 secured between two bone bodies 280 and 290 in accordance with an aspect of the present invention. The bone bodies 280 and 290 can be two adjacent cervical vertebrae and the interbody device 10 can be mounted to the vertebrae with a bone graft (not shown) between the vertebrae. More specifically, the base member 20 of the device 10 is mounted to the vertebrae by attaching the bone fasteners 50, which are located in bone screw holes 140, to one of the cervical vertebrae 280 to be stabilized and the bone fastener 50, which is located in slot 180, to the other of the cervical vertebrae 290 to be stabilized. The base member 20 is positioned such that the first and second legs 120, 130 lie generally opposite the bone graft between the two vertebrae. The bone fasteners 50 are driven into the vertebrae 280, 290 sufficiently so that the convex spherical configuration of the bone fasteners 50 bear against the seats 165 of the bone screw holes 140 and secure the base member 20 against anterior surfaces of the two cervical vertebrae 280, 290. More specifically, the bone fasteners 50 provided through the bone screw holes 140 are driven through an end surface of bone body 280; and the bone fastener 50 provided through the slot 180 is driven through a top surface of bone body 290.

To provide an enhanced fit, a few millimeters of bone can be trimmed or otherwise removed from a lip osteophyte of the second vertebral body 290 at an angle corresponding to the angle of the secondary member 110 of the base member 20. The trimmed surface provides a substantially flat surface 300 for anchoring the bone screw 50 into the lip osteophyte of the second vertebral body 290 The surface also accommodates sliding of the tab as the teeth subside into the second vertebral body 290.

The angles of the bone screws 50 relative to the bone surfaces of the vertebral bodies 280, 290 are important. The lip osteophyte is the strongest part of the bone, and thus angling the bone screws 50 through the lip osteophyte increases the ability of the base member 20 to stay anchored to the vertebral bodies 280, 290. Moreover, by being angled, each bone screw 50 is positioned along an angle of rotation of a corresponding vertebral body 280, 290 as well as an angle of settling of the vertebral body 280, 290. This places each screw 50 in a protected position against motion of the spinal column. As a result, significant sheer forces are not exerted on the screws 50 as the vertebral bodies 280, 290 rotate and settle.

Figure 13:
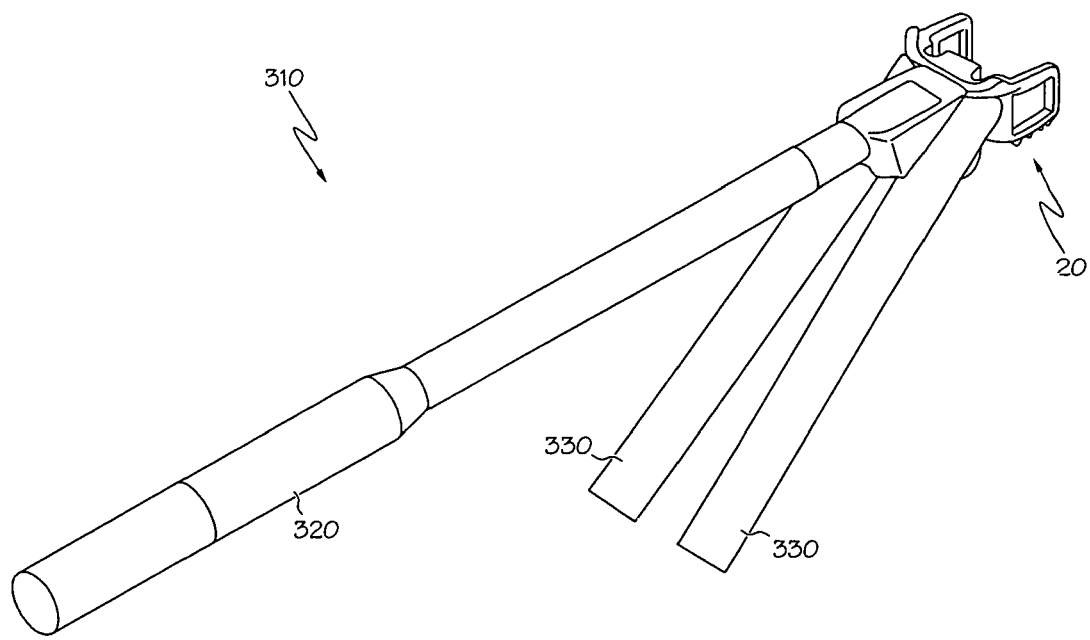
FIG. 13 is a perspective view of a guide tube system for inserting bone screws into a base member of an interbody device in accordance with an aspect of the present invention.

A first guide tool 310 as illustrated in FIG. 13 can be provided to allow a surgeon to hold and position the base member 20 against the bone, and to accurately drill into the bone. The guide tool 310 includes a handle 320 for holding and manipulating a position of the guide tool 310. A projection (not shown) extends from a base portion of the guide tool 310 and is configured to engage hole 170 in the primary member 100 of the base 20 to hold the guide tool 310 in position. When the handle 320 is properly engaged with the base member 20, a pair of guide tubes 330 is properly lined up with corresponding bone screw holes 140. The surgeon then inserts a drill or center punch (not shown) through one of the guide tubes 330 to drill a hole in the bone, through the screw hole 140. Then, after removing the drill, the surgeon inserts a bone screw 50 held at the end of a suitable driver (not shown) through the guide tube 330, and screws it into the bone. The process is repeated until the desired number of screws are placed, leaving the base member secured to the bone via the first bone screw holes 140. Or, since the first guide tool 310 includes two guide tubes 330, the bone screws 50 can be inserted at substantially the same time.

Figure 14:
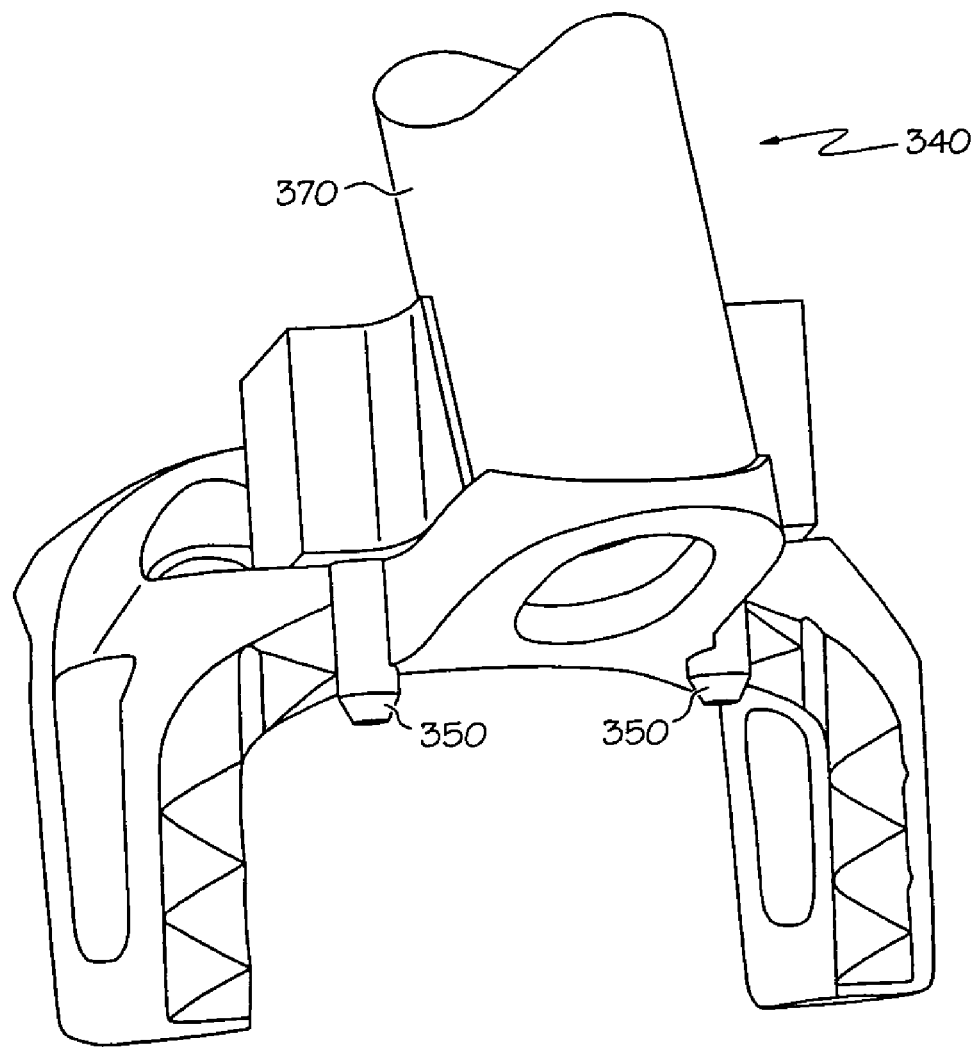
FIG. 14 is a bottom perspective view of another guide tube system for inserting a bone screw into a base member of an interbody device in accordance with an aspect of the present invention.

A second guide tool 340 is illustrated in FIG. 14 is also provided to allow a surgeon to hold and position the base member 20 against the bone, and to accurately drill into the bone. More specifically, the second guide tool 340 is employed to drill a bone screw 50 into the bone slot 180. The second guide tool 340 includes two substantially round projections 350 that engage corresponding notches 360 provided between the secondary member 110 of the base 20 and an adjacent interface member 30 provided on each side of the secondary member 110 (see FIGS. 4 and 5) to hold the second guide tool 340 in position. As above, the surgeon then inserts a drill (not shown) through a guide tube 370 to drill a hole in the bone, through the screw slot 180. Then, after removing the drill, the surgeon inserts a bone screw 50 held at the end of a suitable driver (not shown) through the guide tube 370, and screws it into the bone. It should be noted that one function of the guide is to locate the screw at the end of the slot so the screw travel can match subsidence of the teeth. If for example the screw was placed in the center of the slot it would bottom out in the slot before the teeth had fully embedded.

Turning back to FIGS. 11 and 12, once the bone screws 50 are inserted into the bone screw holes 140 and the bone screw slot 180, the restraining plate 60 is placed over the base member and fixed in place to prevent the screws 50 from "backing out" of the screw holes 140, 180. The second bone screw 50 that extends through the bone screw slot 180 is nonetheless permitted to slide along the length of the slot 180, even when the restraining plate 60 is secured in place. Thus, second the bone screw 50 and the bone screw slot 180 cooperate to control any lateral or rotary movement of one vertebral body relative to an adjacent vertebral body during "settling" of the bone. Further, the angled orientation of the second member 110 provides the base member 20 with resilient properties, for example, enabling the base member 20 "flex" when one vertebra is rotated relative to an adjacent vertebrae.

As noted above, all of the bone screws 50 are preferably permitted to toggle, or pivot, even after the restraining plate 60 is fixed over the base member 20. The ability of the screws 50 to toggle permits the interbody device 10 to migrate and self-center after it has been implanted.

The base member 20 is configured such that when first installed on the cervical vertebrae, the interface members 30 contact a surface of at least one of the bone bodies. For instance, in the present example, the base member 20 is positioned between the vertebrae 280 and 290 such that the top surface 150 of the base member 20 contacts an end surface of one vertebral body 280 and the interface members 30 contact an end surface of the other vertebral body 290. As discussed above, the interface members 30 are configured such that substantially immediate penetration does not occur. Rather, the interbody device 10 gradually subsides as the vertebrae and bone graft fuse to share in the weight bearing during settling of the vertebral bodies. Specifically, as the vertebral bodies move toward each other during settling, the interface members 30 will contact and enter the second vertebral body 290 with increased resistance to subsidence. This contact controls the rate of settling.

The interbody device 10 provides such an interface design by controlling the height, size, shape, and spacing of the teeth that interdigitate with the endplate of the vertebral body. In addition screw fixation is provided. The length of screw travel in the slot 180 is matched to the height of the interface members 30. Accordingly, subsidence is arrested once the bone screw 50 reaches the intended limit as provided by the slot 180. Screw fixation also addresses expulsion of the interbody device, a concern common to all interbody devices. The interbody device 10 accommodates a large graft surface area further increasing the probability that fusion will occur.

As shown in FIG. 12, the interbody device 10 of the present invention has a substantially low profile. Namely, the base member of the present invention is designed to have an outer periphery that coincides with or generally matches the outer diameter of the cortex. The top surface of the base sits at, and preferably below, the top surface of the vertebral bodies. As such, the interbody device 10 of the present invention does not have any parts that would significantly interfere with or irritate the trachea, esophagus, and/or other anatomic structures of the user.

Another advantage of the interbody device 10 is that it is stackable. Frequently after a bone graft is inserted and a bone plate joined to the surrounding vertebral bodies, for example, C4 and C5, an adjacent disk, for example, between C5 and C6, subsequently deteriorates. With traditional bone plates, it would be necessary to remove the plate from C4-C5 before attaching a second bone plate to C5 and C6 because each plate covers a significant surface of the vertebral body. To remove a bone plate, it is necessary dissect scar tissue, which can have a negative impact on the patient. In contrast, the interbody device 10 of the present invention covers an insignificant portion of the top surfaces of the vertebral bodies to which it is attached, instead being located primarily between the vertebral bodies. As a result, multiple interbody devices can be introduced over adjacent bone grafts (i.e., between a common vertebral body) so that two interbody devices are attached to a common vertebral body without the bone plate systems contacting one another. Thus, subsequent procedures where new bone grafts are to be inserted do not require the removal of a pre-existing device prior to introduction of a new device. The depicted systems where the bone screws are provided in a generally triangular arrangement further enhance the stacking ability of the interbody devices of the invention.

Figure 15:
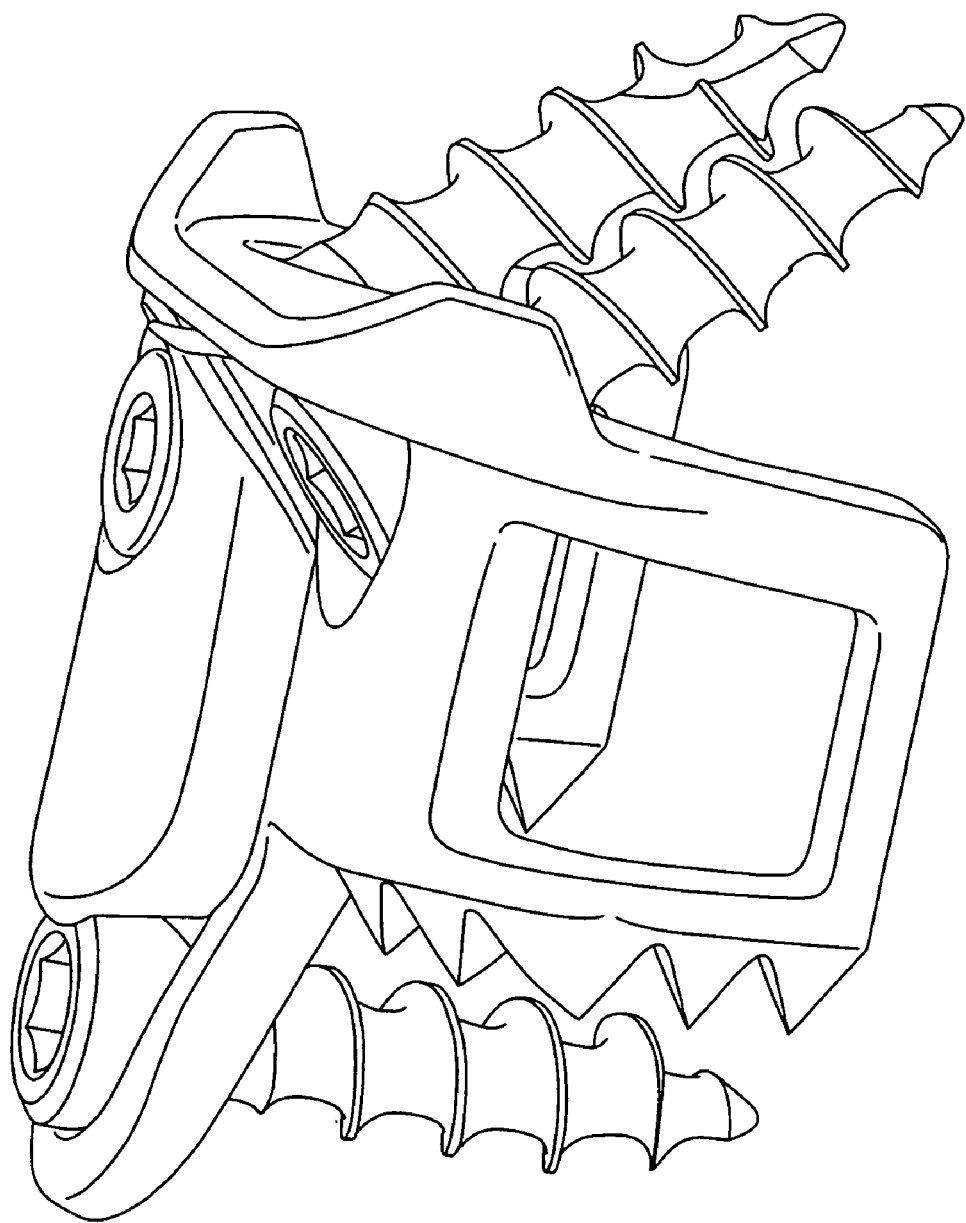
FIG. 15 is a side perspective view of another interbody device in accordance with an aspect of the present invention.
Figure 16:
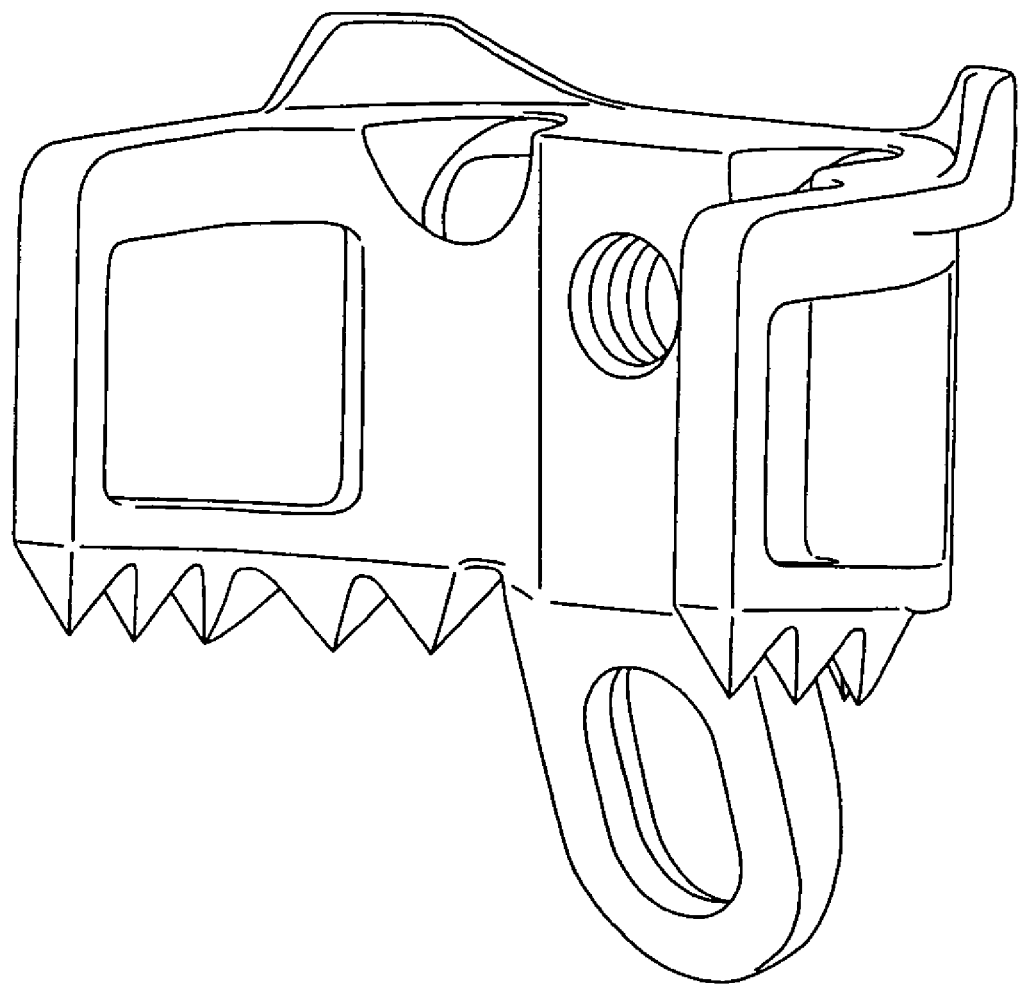
FIG. 16 is a back perspective view of another base member of an interbody device in accordance with an aspect of the present invention.

It is to be appreciated that a kit having base plates of different sizes, bone screws of differing lengths and restraining plates complementary to the base plates can be provided. For instance, because of the different physical dimensions of the patients on whom the invention is used, it is preferable that bone plate systems of correlative dimensions be available. The present invention is capable of being provided in various sizes for that purpose. FIGS. 15 and 16 illustrate examples of a base member and interbody device, respectively, having a larger size than the interbody device 10 described with respect to FIGS. 1-13. The kit may further comprise a tack tool, a drilling tool, tapping tool and/or one or more screw driving tools.

While preferred embodiments of the present invention are described for supporting adjacent cervical vertebrae in the anterior region of the vertebrae, persons skilled in the art would recognize that the bone plate of the present invention may be utilized to support adjoining thoracic and lumbar vertebrae in the lateral or posterior regions of the vertebrae. Further, the device and method of the invention is not limited to vertebral bodies, but can also be use to join two other pieces of bone in other parts of the body.

While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. An interbody device comprising:
    a base member having a plurality of interface members extending from a portion of the base member, the interface members configured to provide controlled subsidence of the interbody device into a bone body over a period of time subsequent to implantation adjacent to the bone body;
    a plurality of bone fasteners extending through apertures provided in the base member; and
    restraining means for restricting movement of at least one of the plurality of bone fasteners;
    wherein the apertures provided in the base member includes an elongated slot configured to receive a bone fastener therethrough, the plurality of interface members have a dimensional extension adapted to penetrate into the bone body during the controlled subsidence, and the slot having an elongation dimension along which the bone fastener extending therethrough moves as a whole along the elongate dimension during the controlled subsidence.

2. The interbody device of claim 1, wherein the plurality of interface members includes a plurality of teeth.

3. The interbody device of claim 1, wherein the plurality of interface members includes at least one of teeth, knife-edges, spikes, posts, and pegs extending from a bottom surface of the base member.

4. The interbody device of claim 1, wherein the restraining means includes a restraining plate and a restraining plate fixing means.

5. The interbody device of claim 4, wherein the restraining plate engages the plurality of bone fasteners and is configured to restrict movement of all of the plurality of bone fasteners.

6. The interbody device of claim 4, wherein the restraining plate includes a U-shaped notch curved outwardly towards an edge of the restraining plate, with at least a portion of the bone fastener is located within the U-shaped notch and moving within the U-shaped notch during the movement of the bone fastener along the slot during controlled subsidence.

7. The interbody device of claim 4, wherein plurality of bone fasteners is exactly three bone fasteners, the base member has exactly three bone fastener receiving apertures through which the three bone fasteners are received and extend, exactly two of the three bone fastener receiving apertures are non-elongated and exactly one of the three bone fastener receiving apertures is the elongate slot, the restraining means includes exactly one restraining plate that covers all three bone fasteners.

8. The interbody device of claim 1, wherein the base member includes a primary member and a secondary member, the secondary member extending from and being angled relative to the primary member, the elongated slot being located within the secondary member.

9. The interbody device of claim 8, wherein the angle between the primary member and the secondary member is between 90-degrees and 180-degrees for permitting the primary member to engage a first part of the bone body and the secondary member to engage a second, different part of the bone body away from the first part of the bone body.

10. The interbody device of claim 8, wherein the angle between the primary member and the secondary member is between 110-degrees and 160-degrees for permitting the primary member to engage a first part of the bone body and the secondary member to engage a second, different part of the bone body away from the first part of the bone body.

11. The interbody device of claim 1, wherein the interface members are configured to subside into one or more bone bodies in accordance with a desired subsidence profile to a depth that is substantially equivalent to a height of the interface members.

12. The interbody device of claim 1, wherein a shape of the interface members controls a rate of subsidence of the interbody device into an adjacent bone body.

13. The interbody device of claim 1, further comprising a shelf-like area created at an interface between a bottom surface of the base member and the plurality of interface members extending from the bottom surface of the base member.

14. The interbody device of claim 1, wherein the apertures provided in the base member includes at least one angled hole different from the elongate slot and configured to receive a corresponding bone fastener therethrough.

15. The interbody device of claim 14, wherein the apertures provided in the base member include two angled holes different from the elongate slot and having generally concave spherical seats to allow the corresponding bone fasteners provided therethrough to pivot on the seats.

16. The interbody device of claim 1, wherein the base member includes at least one projection extending from a top surface of the base member, the at least one projection configured to contact a surface of at least one of the bone bodies to provide a stop during insertion of the interbody device between the bone bodies.

17. The interbody device of claim 1, wherein the base member is substantially U-shaped and comprising a primary member, a secondary member angled with respect to the primary member, and a first and second leg, the first and second legs configured to fit between end portions of the bone bodies.

18. The interbody device of claim 17, wherein the first and second legs have apertures configured to provide bone growth therethrough.

19. The interbody device of claim 1, wherein the plurality of interface members have elongation oriented in the same direction as the elongation of the slot and the bone fastener is located within the slot so that the bone fastener travel matches penetration subsidence of the plurality of interface members into the bone body.

20. The interbody device of claim 1, wherein the dimensional extension of the plurality of interface members is matched to be the same as the elongation dimension of the slot such that bone fastener reaches an end of the slot as the dimensional extension of the plurality of interface members completes penetration into the bone body.

21. The interbody device of claim 1, wherein relative sliding movement and relative pivoting movement occurs between at least one of the plurality of bone fasteners and the base member during the controlled subsidence.

22. The interbody device of claim 1, wherein no relative sliding movement occurs between at least one fastener and the base member.

23. The interbody device of claim 1, wherein no relative sliding movement occurs between at least some of the plurality of bone fasteners and the base member.

24. The interbody device of claim 1, wherein the controlled subsidence is associated with a dimension of penetration of at least one interface member into the bone body, and at least one bone fastener having a dimension of displacement relative to the base member that is within a range that includes no displacement and also does not include a dimension of displacement that equals the dimension of penetration.

25. The interbody device of claim 1, wherein at least one interface member has a dimension that is adapted to be fully penetrated into the bone body at some point along the controlled subsidence.

26. The interbody device of claim 25, wherein the at least one interface member is adapted to be fully penetrated into the bone body at completion of the controlled subsidence.

27. The interbody device of claim 1, wherein relative sliding movement occurs between at least one fastener and the base member as at least part of the movement during the controlled subsidence, and the relative sliding is arrested at some point along the controlled subsidence.

28. The interbody device of claim 27, wherein the relative sliding is arrested at completion of the controlled subsidence.

29. The interbody device of claim 1, wherein the interface members are located only on a single side of the base member and extend from a surface of the base member only toward the bone body and the device does not include any interface members located on an opposite side of the base member.

30. The interbody device of claim 1, wherein the device is configured to provide that the movement of one the plurality of bone fasteners includes both sliding movement and toggling movement.

31. An interbody device comprising:
  a base member configured for insertion between two adjacent bone bodies;
  controlled subsidence means extending from the base member, the controlled subsidence means configured to provide controlled penetration of the base member into at least one of the bone bodies over a period of time subsequent to the insertion between the bone bodies; and
  means for fastening the base member to the two adjacent bone bodies;
  wherein the means for fastening and the controlled subsidence means includes a bone screw located in an elongate slot through the base member and moving along the elongation of the slot during the subsidence.

32. The interbody device of claim 31, further comprising restraining means secured to the base member which engages the bone screw for restricting movement of the bone screw, wherein the restraining means is configured to restrictively permit at least one of a sliding and toggling movement of the bone screw when secured to the base member including permitting the bone screw to restrictively slide along the slot.

33. The interbody device of claim 31, wherein the controlled subsidence means includes an interface member for penetration into one of the bone bodies during the subsidence, and the bone screw is located within the slot so the screw movement to an end of the slot coincides with complete penetration of the interface member into the bone body.

34. The interbody device of claim 31, wherein the movement along the slot is relative sliding movement.

35. The interbody device of claim 31, wherein the means for fastening includes a plurality of bone fasteners, and no relative sliding movement occurs between at least some of the plurality of bone fasteners and the base member.

36. The interbody device of claim 31, wherein the means for fastening includes a plurality of bone fasteners, and no relative sliding movement occurs between at least some of the bone fasteners and the base member.

37. The interbody device of claim 31, wherein the controlled penetration is associated with a dimension of penetration of at least one interface member into the bone body, and the means for fastening including at least one bone fastener having a dimension of displacement relative to the base member that is within a range that includes no displacement and also does not include a dimension of displacement that equals the dimension of penetration.

38. The interbody device of claim 31, wherein the controlled subsidence means includes at least one interface member that has a dimension that is adapted to be fully penetrated into the bone body at some point along the controlled subsidence.

39. The interbody device of claim 38, wherein the at least one interface member is adapted to be fully penetrated into the bone body at completion of the controlled subsidence.

40. The interbody device of claim 31, wherein the movement along the slot is arrested at some point along the controlled subsidence.

41. The interbody device of claim 40, wherein the relative sliding is arrested at completion of the controlled subsidence.

42. The interbody device of claim 31, wherein the means for fastening and the controlled subsidence means includes bone screws that number exactly three, the device further includes a restraining plate that restricts movement of the bone screws, and the restraining plate includes a U-shaped notch curved outwardly towards an edge of the restraining plate, with at least a portion of one of the bone screws located within the U-shaped notch and moving within the U-shaped notch during the movement of the bone screw along the slot during controlled subsidence.

43. The interbody device of claim 31, wherein the interface members are located only on a single side of the base member and extend from a surface of the base member only toward one of the bone bodies and do not extend toward the other of the bone bodies.

44. The interbody device of claim 31, wherein at least one of the interference members are substantially symmetrical in each of two perpendicular directions.

45. The interbody device of claim 31, wherein at least one of the interference members applies substantially symmetrical penetration force to the at least one of the bone bodies during the controlled penetration.

46. The interbody device of claim 31, wherein the device is configured to provide that the movement of the bone fastener includes both sliding movement and toggling movement.

47. An interbody device comprising:
a base member configured for insertion between two adjacent bone bodies, the base member comprising:
a plurality of interface members extending from a surface of the base member, the plurality of interface members configured to provide a controlled penetration of the base member into at least one surface of at least one of the body bodies over a period of time subsequent to the insertion between the two bone bodies;
at least one angled hole extending therethrough for receiving a bone fastener; and
at least one elongated slot extending therethrough for receiving a bone fastener, the elongated slot configured to permit the corresponding bone fastener to slide within the slot, the at least one elongated slot being of a different configuration from the at least one angled hole.

48. The interbody device of claim 47, wherein the at least one angled hole is configured to permit the corresponding bone fastener to toggle within the angled hole, with the pivoting of the corresponding bone fastener in the at least one angled hole being different from the sliding of the corresponding bone fastener within the elongated slot.

49. The interbody device of claim 47, wherein the at least one angled hole is configured to direct the corresponding bone fastener through an end surface of one of the bone bodies.

50. The interbody device of claim 49, wherein the at least one elongated slot is configured to direct the corresponding bone fastener through a top surface of the other of the bone bodies.

51. The interbody device of claim 47, further comprising a retaining plate secured to the base member via a fastener to mitigate backing out of the bone fasteners from the bone bodies, and including a portion engaging the corresponding bone fastener extending through the elongated slot, the bone fastener sliding along the retaining plate during sliding of the bone fastener within the elongated slot to provide resistance to the sliding with the sliding along the retaining plate being the same as the sliding along the elongated slot.

52. The interbody device of claim 51, wherein the retaining plate includes a surface having at least one rounded notch formed therein that corresponds to a position of the bone fastener provided through the at least one angled hole, the at least one rounded notch permitting toggling of the bone fastener within the at least one angled hole while preventing backing out of the bone fastener from the bone body.

53. The interbody device of claim 51, wherein the retaining plate includes a surface having at least one U-shaped notch formed therein that corresponds to a position of the bone fastener provided through that at least one elongated slot, the at least one U-shaped notch permitting sliding of the bone fastener within the slot while preventing backing out of the bone fastener from the bone body.

54. The interbody device of claim 47, wherein a sliding extent of the bone screw within the elongate slot corresponds to a penetration extent of the plurality of interface members into the at least one of the body bodies.

55. The interbody device of claim 47, further comprising at least one bone fastener that does not slide relative to the base member.

56. The interbody device of claim 47, wherein the controlled subsidence is associated with a dimension of penetration of at least one interface member into the bone body, and the bone fastener slides within the slot for at least a portion of a distance that corresponds to the dimension of penetration.

57. The interbody device of claim 56, wherein the bone fastener slides within the slot for the distance that corresponds to the dimension of penetration.

58. The interbody device of claim 47, wherein at least one interface member is adapted to be fully penetrated into the bone body at a point during the controlled subsidence.

59. The interbody device of claim 58, wherein the point of full penetration is at completion of the controlled subsidence.

60. The interbody device of claim 58, wherein sliding of the bone fastener within the slot is arrested at some point along the controlled subsidence.

61. The interbody device of claim 60, wherein the sliding is arrested at completion of the controlled subsidence.

62. The interbody device of claim 47, wherein the interface members are located only on a single side of the base member and extend from the surface of the base member only toward one of the bone bodies and do not extend toward the other of the bone bodies.

63. The interbody device of claim 47, wherein at least one of the interference members are substantially symmetrical in each of two perpendicular directions.

64. The interbody device of claim 47, wherein at least one of the interference members applies substantially symmetrical penetration force to the at least one of the bone bodies during the controlled penetration.

65. A device for fixation and support of bone bodies comprising:
a body configured to interface with two or more bone bodies and having an elongate slot; and
at least one interface member extending from the body;
at least one fastener extending lengthwise transversely through the elongate slot;
wherein the at least one interface member and the at least one fastener are configured to provide a controlled subsidence of the body into at least one of the two or more bone bodies over a period of time subsequent to implantation between the bone bodies, including relative sliding movement between the at least one fastener and the body such that the at least one fastener moves transverse to a direction of its length along the elongation of the elongate slot.

66. The device of claim 65, wherein the configuration of the at least one interface member affects a relationship between an applied load by the at least one interface member and an amount of settling of the at least one interface member into the at least one of the two or more bone bodies.

67. The device of claim 65, wherein the height of the at least one interface member determines a depth of penetration into the one of the two or more bone bodies.

68. The device of claim 65, wherein an interface between the body and the at least one interface member includes a shelf-like area to increase subsidence resistance when the at least one interface member has fully subsided into the one of the two or more bone bodies.

69. The device of claim 68, wherein the at least one fastener includes a bone screw located in a slot through the body, the slot having an end and the bone screw being at the end when the at least one interface member has fully subsided into the one of the two or more bone bodies.

70. The device of claim 65, wherein the at least one interface member includes at least one tooth such that as the tooth becomes wider in cross section, the tooth is adapted such that penetration of the tooth into the at least one bone body will become slower.

71. The device of claim 65, wherein the at least one bone fastener non-pivotally slides along the elongate slot in the body.

72. The device of claim 71, wherein the at least one bone fastener includes a plurality of bone fasteners and for at one of which no relative sliding movement occurs relative to the body.

73. The device of claim 72, wherein for the plurality of bone fasteners at least two of the bone fasteners have no relative sliding relative to the body.

74. The interbody device of claim 72, wherein the at least one bone fastener includes a plurality of bone fasteners and no relative sliding occurs between at least one of plurality of bone fasteners and the base member during the progressive penetration.

75. The device of claim 65, wherein the controlled subsidence is associated with a dimension of penetration of at least one interface member into the bone body, and a dimension of displacement of the at least one fastener relative to the body that is within a range that includes no displacement and also does not include a dimension of displacement that equals the dimension of penetration.

76. The device of claim 65, wherein at least one interface member has a dimension that is adapted to be fully penetrated into the bone body at some point along the controlled subsidence.

77. The device of claim 76, wherein the at least one interface member is adapted to be fully penetrated into the bone body at completion of the controlled subsidence.

78. The device of claim 65, wherein the relative sliding is arrested at some point along the controlled subsidence.

79. The device of claim 78, wherein the relative sliding is arrested at completion of the controlled subsidence.

80. A device for fixation and support of bone bodies comprising:
means for interfacing between two or more bone bodies; and
means for providing a controlled subsidence of the device into at least one of the two or more bone bodies in accordance with a desired subsidence profile over a period of time subsequent to the implantation the two bone bodies;
wherein the means for providing a controlled subsidence and the means for interfacing include a bone screw located in an elongate slot for retaining the device to one of the bone bodies and an interface member for penetration into one of the bone bodies, the elongate slot having an end and a desired subsidence profile ends when the interference member is at a maximum penetration and the bone screw is at the end of the slot.

81. The device of claim 80, wherein the means for interfacing includes a base member with the slot being located in the base member at a location extending along one of the bone bodies at a location facing away from the other of the bone bodies.

82. The device of claim 81, wherein relative sliding movement occurs between the bone screw and the base member during the controlled subsidence, with the bone screw having an elongation and the sliding of the bone screw being transverse to the direction of elongation of the bone screw.

83. The device of claim 81, wherein a second bone screw is provided and the first bone screw and the second bone screw interact differently with the base member to provide that no relative sliding movement occurs between the second bone screw and the base member.

84. The device of claim 83, wherein a third bone screw is provided and the first bone screw and the third bone screw interact differently with the base member to provide that no relative sliding movement occurs between the third bone screw and the base member.

85. The device of claim 80, wherein the means for providing controlled subsidence includes means for penetrating into the at least one of the two or more bone bodies during relative movement of the two or more bone bodies.

86. The device of claim 85, wherein at least one of the interference members are substantially symmetrical in each of two perpendicular directions.

87. The device of claim 85, wherein at least one of the interference members applies substantially symmetrical penetration force to the at least one of the bone bodies during the controlled penetration.

88. The device of claim 80, wherein the means for interfacing includes a body of the device, and the means for providing controlled subsidence includes a plurality of screws that move relative to the body of the device during relative movement of the two or more bone bodies.

89. The device of claim 80, wherein the means for providing a controlled subsidence and the means for interfacing include a bone screw includes exactly three bone screws, the device further includes a restraining plate that restricts movement of the bone screws, and the restraining plate includes a U-shaped notch curved outwardly towards an edge of the restraining plate, with at least a portion of the bone screw extending through the slot being located within the U-shaped notch and moving within the U-shaped notch during the sliding of the bone screw along the slot during controlled subsidence.

90. A device for securing two adjacent spinal vertebrae, the device comprising:
a body for implantation at a location between the two vertebrae, an aperture provided in the body;
at least one protrusion extending from the body for engagement with one of the vertebrae upon implantation and for progressive penetration into the vertebra over a period of time subsequent to the implantation; and
at least one bone fastener extending through the aperture in the body and the body and the at least one bone fastener configured for relative sliding movement between the at least one bone fastener and the body during the controlled subsidence, the sliding is non-pivoting movement.

91. The device as set forth in claim 90, wherein the protrusion extends from the body in a direction that is aligned with an elongate direction of the spine.

92. The device as set forth in claim 91, wherein the protrusion is configured to provide increased resistance to penetration as the protrusion penetrates into the vertebra.

93. The device as set forth in claim 90, wherein the protrusion is configured to provide increased resistance to penetration as the protrusion penetrates into the vertebra.

94. The device of claim 90, wherein the at least one bone fastener includes a bone screw located and the aperture includes a slot, the bone screw for retaining the device to one of the two vertebrae, wherein the duration of the period of time for progressive penetration extends while the bone screw is sliding and until the protrusion is fully penetrated into the one vertebra and the screw is at an end of the slot.

95. The device of claim 90, wherein the at least one bone fastener includes first and second bone fasteners, the first bone fastener is configured for the sliding movement relative to the body during the controlled subsidence, and the first bone fastener and the second bone fastener interact differently with the body to provide that no relative sliding movement occurs between the second bone fastener and the body.

96. The device of claim 95, wherein the at least one bone fastener further includes a third bone fastener, and the first bone fastener and the third bone fastener interact differently with the body to provide that no relative sliding occurs between the third bone fastener and the body.

97. An interbody device for securing two adjacent bone members, the device comprising:
a base member for implantation at a location between the two bone members; and
means for maintaining the base member within the implant location between the bone members;
wherein the means for maintaining includes at least one bone fastener extending through an elongate aperture provided in the base member for securing into one of the bone members at a point outside of the location between the two bone members, the base member includes at least one protrusion for engagement with one of the bone members upon implantation and for progressive penetration over a period of time subsequent to the implantation, relative sliding movement occurs between the at least one bone fastener and the base member during the progressive penetration, the relative sliding includes the at least one bone fastener and the point of the securing of the at least one bone fastener relative to the elongate aperture.

98. The interbody device of claim 97 further including a bone fastener for securing into one of the bone members at a point within the location between the two bone members and that has no relative sliding movement during the progressive penetration.

\* \* \* \* \*